United States Patent
Hantash

(10) Patent No.: US 12,414,978 B2
(45) Date of Patent: Sep. 16, 2025

(54) TYROSINE INHIBITORS WITH IMMUNOSUPPRESSIVE ACTIVITY IN HUMAN NEONATAL KERATINOCYTE PROGENITORS

(71) Applicant: ESCAPE THERAPEUTICS, INC., Turlock, CA (US)

(72) Inventor: Basil M. Hantash, Turlock, CA (US)

( * ) Notice: Subject to any disclaimer, the term of this patent is extended or adjusted under 35 U.S.C. 154(b) by 750 days.

(21) Appl. No.: 17/420,396

(22) PCT Filed: Jan. 20, 2020

(86) PCT No.: PCT/US2020/014298
§ 371 (c)(1),
(2) Date: Jul. 2, 2021

(87) PCT Pub. No.: WO2020/150718
PCT Pub. Date: Jul. 23, 2020

(65) Prior Publication Data
US 2022/0088116 A1    Mar. 24, 2022

Related U.S. Application Data

(60) Provisional application No. 62/794,582, filed on Jan. 19, 2019.

(51) Int. Cl.
| | | |
|---|---|---|
| *A61K 38/08* | (2019.01) |
| *A61K 31/05* | (2006.01) |
| *A61P 17/00* | (2006.01) |
| *A61P 29/00* | (2006.01) |
| *A61P 37/06* | (2006.01) |
| *C07K 7/06*  | (2006.01) |

(52) U.S. Cl.
CPC .............. *A61K 38/08* (2013.01); *A61K 31/05* (2013.01); *A61P 17/00* (2018.01)

(58) Field of Classification Search
CPC .... A61K 38/08; A61K 9/0019; A61K 9/0053; A61P 17/00; A61P 29/00; A61P 37/06; C07K 7/06
See application file for complete search history.

(56) References Cited

U.S. PATENT DOCUMENTS

| | | | |
|---|---|---|---|
| 7,902,329 B2 * | 3/2011 | Hantash ................. | A61P 17/18 530/328 |
| 8,314,065 B2 * | 11/2012 | Ramaiah ................ | A61P 17/02 514/21.4 |
| 2009/0099091 A1 * | 4/2009 | Hantash ................ | A61P 17/18 530/328 |
| 2018/0296456 A1 * | 10/2018 | Hantash ................ | A61P 17/00 |

FOREIGN PATENT DOCUMENTS

| | | | | |
|---|---|---|---|---|
| WO | WO-2018183882 A1 * | 10/2018 | ............. | A61K 38/08 |

OTHER PUBLICATIONS

Heise, ER., "Diseases Associated with Immunosuppression," Environmental Health Perspectives, 1982, 43: 9-19. (Year: 1982).*

* cited by examiner

*Primary Examiner* — Julie Ha

(57) ABSTRACT

Tyrosine inhibitors having immunosuppressive activity in human neonatal keratinocyte progenitors are described. Particular embodiments feature the immunosuppressive effects of a decapeptide and/or oxyresveratrol, as measured by two different methods: blockade of stimulated cell growth, and inhibition of cytotoxic killing.

13 Claims, 11 Drawing Sheets

Specification includes a Sequence Listing.

SEQUENCE LISTING

<160> NUMBER OF SEQ ID NOS: 12

<210> SEQ ID NO 1
<211> LENGTH: 24
<212> TYPE: DNA
<213> ORGANISM: Homo sapiens

<400> SEQUENCE: 1
gccaatcata agatgttgct gaac                                         24

<210> SEQ ID NO 2
<211> LENGTH: 20
<212> TYPE: DNA
<213> ORGANISM: Homo sapiens

-continued

```
<400> SEQUENCE: 2
aacctccctc atctctaact                                               20

<210> SEQ ID NO 3
<211> LENGTH: 20
<212> TYPE: DNA
<213> ORGANISM: Homo sapiens

<400> SEQUENCE: 3
gttggttaca agatccagac                                               20

<210> SEQ ID NO 4
<211> LENGTH: 20
<212> TYPE: DNA
<213> ORGANISM: Homo sapiens

<400> SEQUENCE: 4
agagctgtga gagaatgaag                                               20

<210> SEQ ID NO 5
<211> LENGTH: 23
<212> TYPE: DNA
<213> ORGANISM: Homo sapiens

<400> SEQUENCE: 5
tcttccatac actttactac ctt                                           23

<210> SEQ ID NO 6
<211> LENGTH: 20
<212> TYPE: DNA
<213> ORGANISM: Homo sapiens

<400> SEQUENCE: 6
cagcttaaac aggagtgaac                                               20

<210> SEQ ID NO 7
<211> LENGTH: 20
<212> TYPE: DNA
<213> ORGANISM: Homo sapiens

<400> SEQUENCE: 7 gacatttta gccatttgtc                                                20

<210> SEQ ID NO 8
<211> LENGTH: 24
<212> TYPE: DNA
<213> ORGANISM: Homo sapiens

<400> SEQUENCE: 8
cggaggttcg aagacgatca gata                                          24

<210> SEQ ID NO 9
<211> LENGTH: 10
<212> TYPE: PRT
<213> ORGANISM: Homo sapiens

<400> SEQUENCE: 9

Tyr Arg Ser Arg Lys Tyr Ser Ser Trp Tyr
1               5                   10

<210> SEQ ID NO 10
<211> LENGTH: 10
```

```
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: N-terminal Palmitoyl
<220> FEATURE:
<221> NAME/KEY: AMIDATION
<222> LOCATION: (10)..(10)

<400> SEQUENCE: 10

Tyr Arg Ser Arg Lys Tyr Ser Ser Trp Tyr
1               5                   10

<210> SEQ ID NO 11
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: N-Terminal Palmitoyl
<220> FEATURE:
<221> NAME/KEY: SITE
<222> LOCATION: (6)..(6)
<223> OTHER INFORMATION: D-isoform
<220> FEATURE:
<221> NAME/KEY: MOD_RES
<222> LOCATION: (10)..(10)
<223> OTHER INFORMATION: AMIDATION

<400> SEQUENCE: 11

Tyr Arg Ser Arg Lys Tyr Ser Ser Trp Tyr
1               5                   10

<210> SEQ ID NO 12
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION

<400> SEQUENCE: 12

Tyr Arg Ser Arg Lys Tyr Ser Ser Trp Tyr
1               5                   10
```

TYROSINE INHIBITORS WITH IMMUNOSUPPRESSIVE ACTIVITY IN HUMAN NEONATAL KERATINOCYTE PROGENITORS

CROSS REFERENCE TO RELATED APPLICATION

This application is a U.S. National Phase of International Application No. PCT/US2020/014298, filed Jan. 20, 2020, which claims priority to U.S. Provisional Patent Application No. 62/794,582, filed Jan. 19, 2019, both of which are incorporated by reference herein in their entirety.

SEQUENCE LISTING

This application incorporates by reference a sequence listing entitled "20200120_ELIXP005_ST25.TXT" (3 kilobytes) which was created Jan. 20, 2020 and filed electronically with this application.

BACKGROUND OF THE INVENTION

This invention relates to the field of novel biological agents.

BRIEF SUMMARY OF THE INVENTION

Embodiments relate to tyrosine inhibitors that exhibit immunosuppressive activity in human neonatal keratinocyte progenitors. Particular embodiments feature the immunosuppressive effects of a decapeptide and/or oxyresveratrol, as measured by two different methods: blockade of stimulated cell growth, and inhibition of cytotoxic killing.

Some embodiments comprise a method of treating a subject that performs immunosuppression of a cell, the method comprising administering to a subject in need thereof a composition comprising an effective amount of one or more peptides, oxyresveratrol, or both, wherein the one or more peptides comprise, SEQ ID NO: 9, SEQ ID NO: 10, SEQ ID NO: 11, or SEQ. ID NO: 12. The cell may be a mammalian cell. The cell may be a skin cell. The administering may comprise oral administration. Various embodiments are described in this patent.

In an embodiment, a method of treating a subject by performing immunosuppression of a cell, the method comprising administering to a subject in need thereof a composition comprising an effective amount of one or more peptides, wherein the one or more peptides comprise, SEQ ID NO: 9, SEQ ID NO: 10, SEQ ID NO: 11, or SEQ. ID NO: 12.

In various embodiments, the peptide consists of SEQ ID NO: 9. The cell is a mammalian cell. The mammalian cell is a skin cell. The mammalian skin cell is a progenitor. The progenitor is an epidermal keratinocyte progenitor, a melanoblast, a fibroblast, a histioblast, or a dendroblast. The administration is by oral administration. The cell is terminally differentiated. The cell is a keratinocyte, a melanocyte, a fibrocyte, a histiocyte, or a dendrocyte. The peptide is present in a concentration of about 1 millimolar or less. The composition further comprises oxyresveratrol.

In an embodiment, a method of treating a subject by performing immunosuppression of a cell, the method comprising administering to a subject in need thereof a composition comprising an effective amount of oxyresveratrol.

In various embodiments, the oxyresveratrol is present in a concentration of between about 0.1 millimolar to about 1.0 millimolar. The composition further comprises an effective amount of one or more peptides, wherein the one or more peptides comprises SEQ ID NO: 9. The cell is a mammalian cell. The mammalian cell is a skin cell. The mammalian skin cell is a progenitor. The progenitor is an epidermal keratinocyte progenitor, a melanoblast, a fibroblast, a histioblast, or a dendroblast. The administration is by oral administration. The cell is a terminally differentiated keratinocyte, melanocyte, fibrocyte, histiocyte, or dendrocyte.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1A:
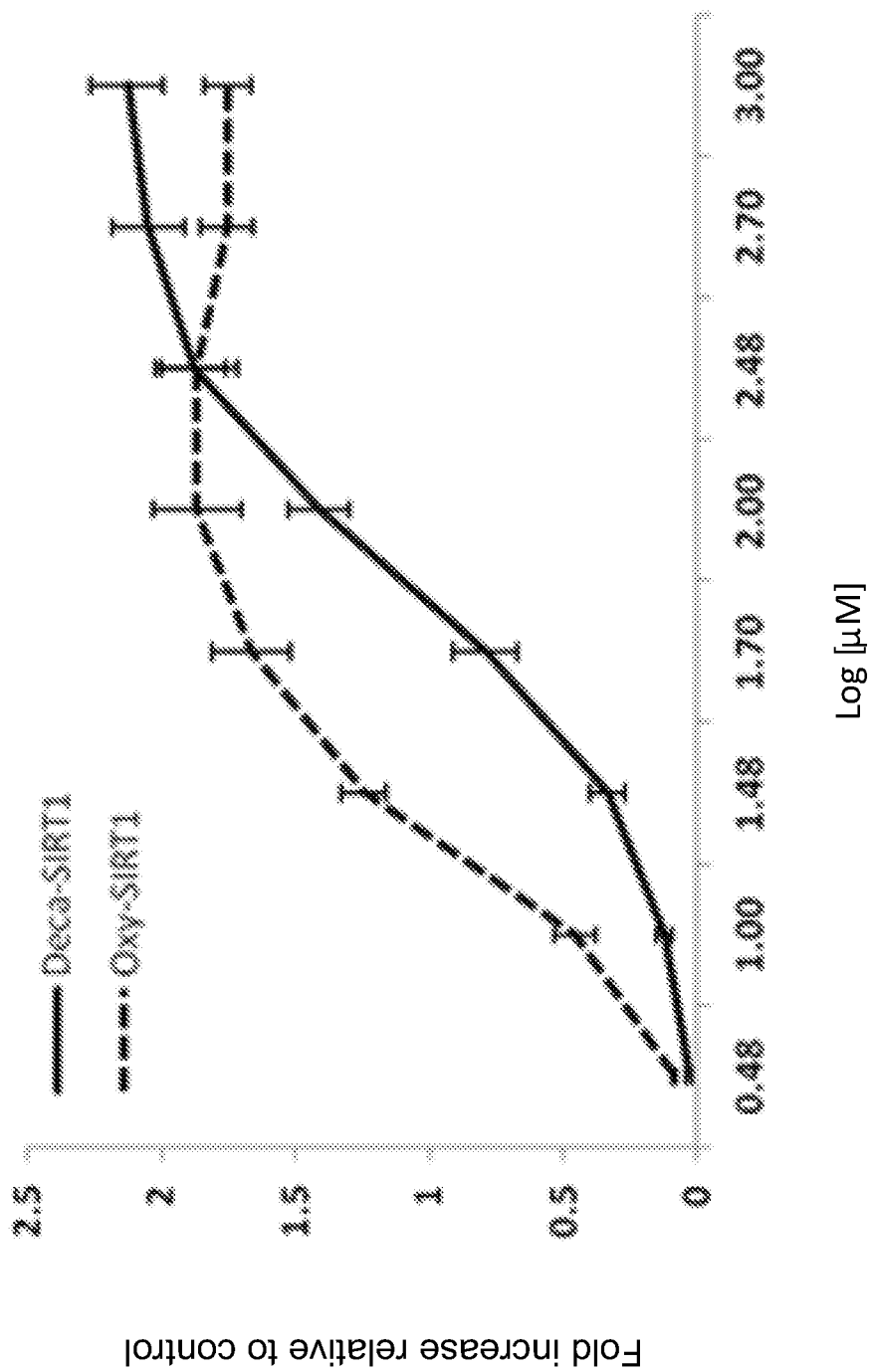
FIG. 1A shows dose-dependent transcriptional upregulation of SIRT1 (a). Data are expressed as fold increase relative to the internal control gene 18S, and represent means±SEM of 3 independent experiments.
Figure 1B:
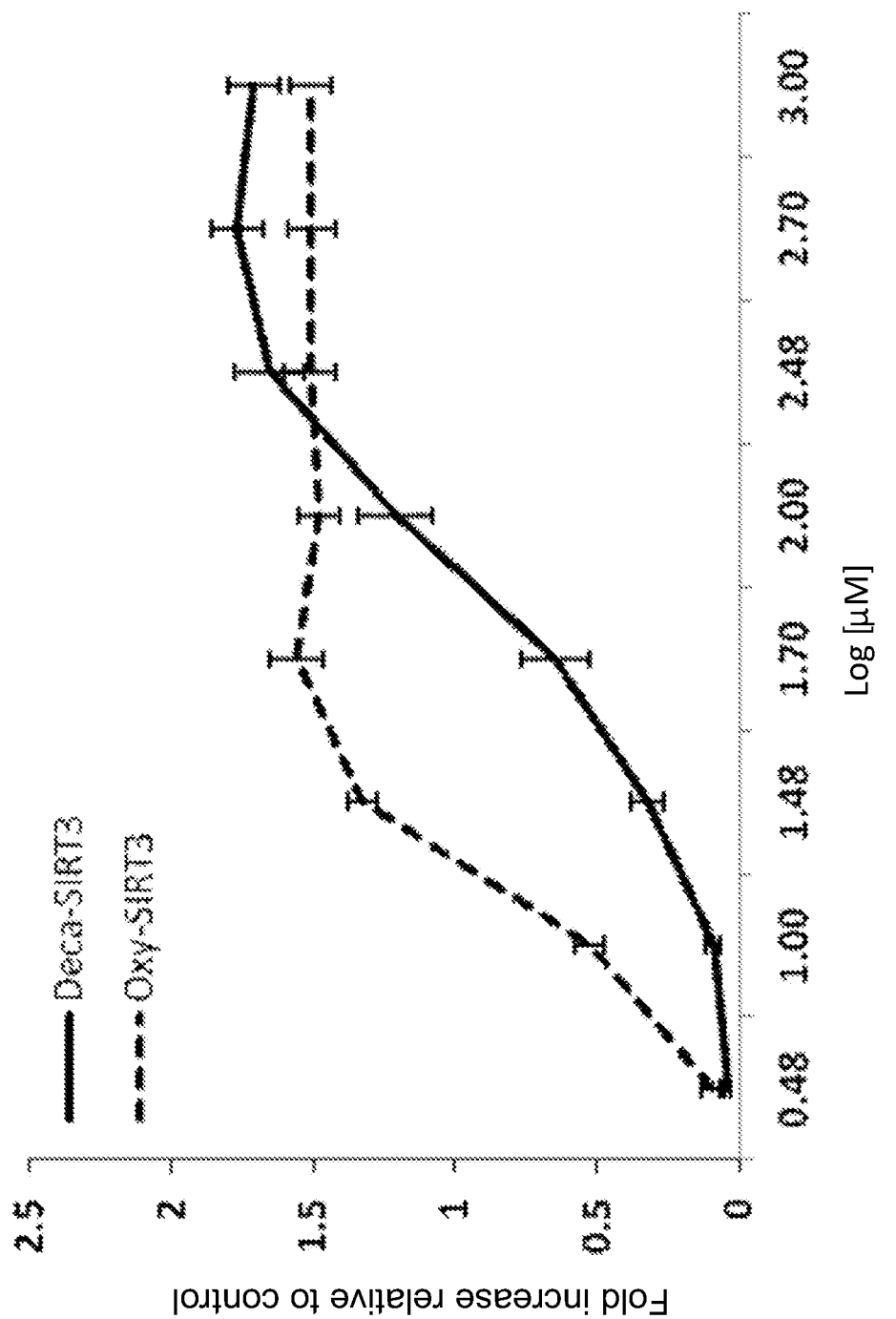
FIG. 1B shows dose-dependent transcriptional upregulation of SIRT3, (b). Data are expressed as fold increase relative to the internal control gene 18S, and represent means±SEM of 3 independent experiments.
Figure 1C:
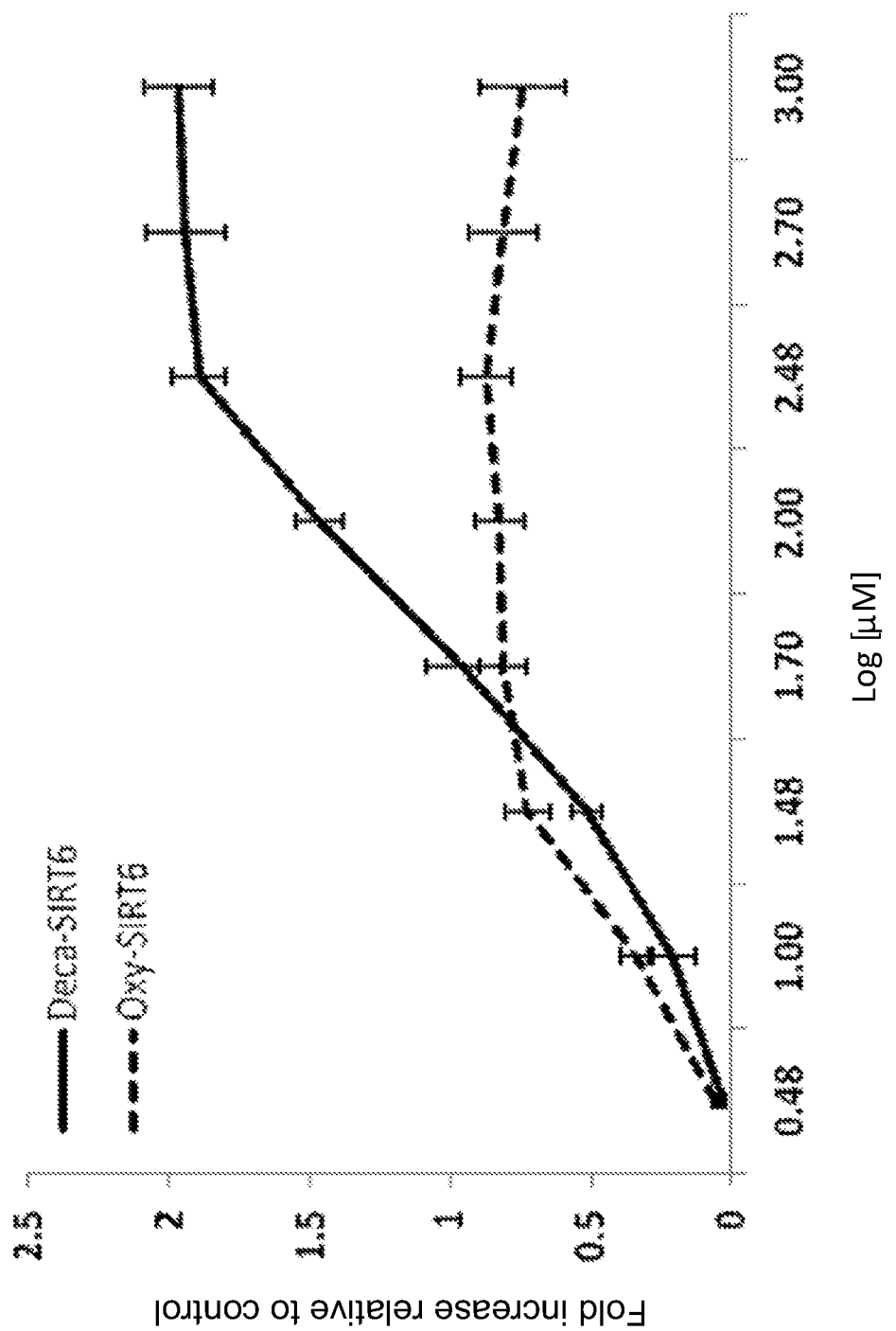
FIG. 1C shows dose-dependent transcriptional upregulation of SIRT6 (c). Data are expressed as fold increase relative to the internal control gene 18S, and represent means±SEM of 3 independent experiments.
Figure 1D:
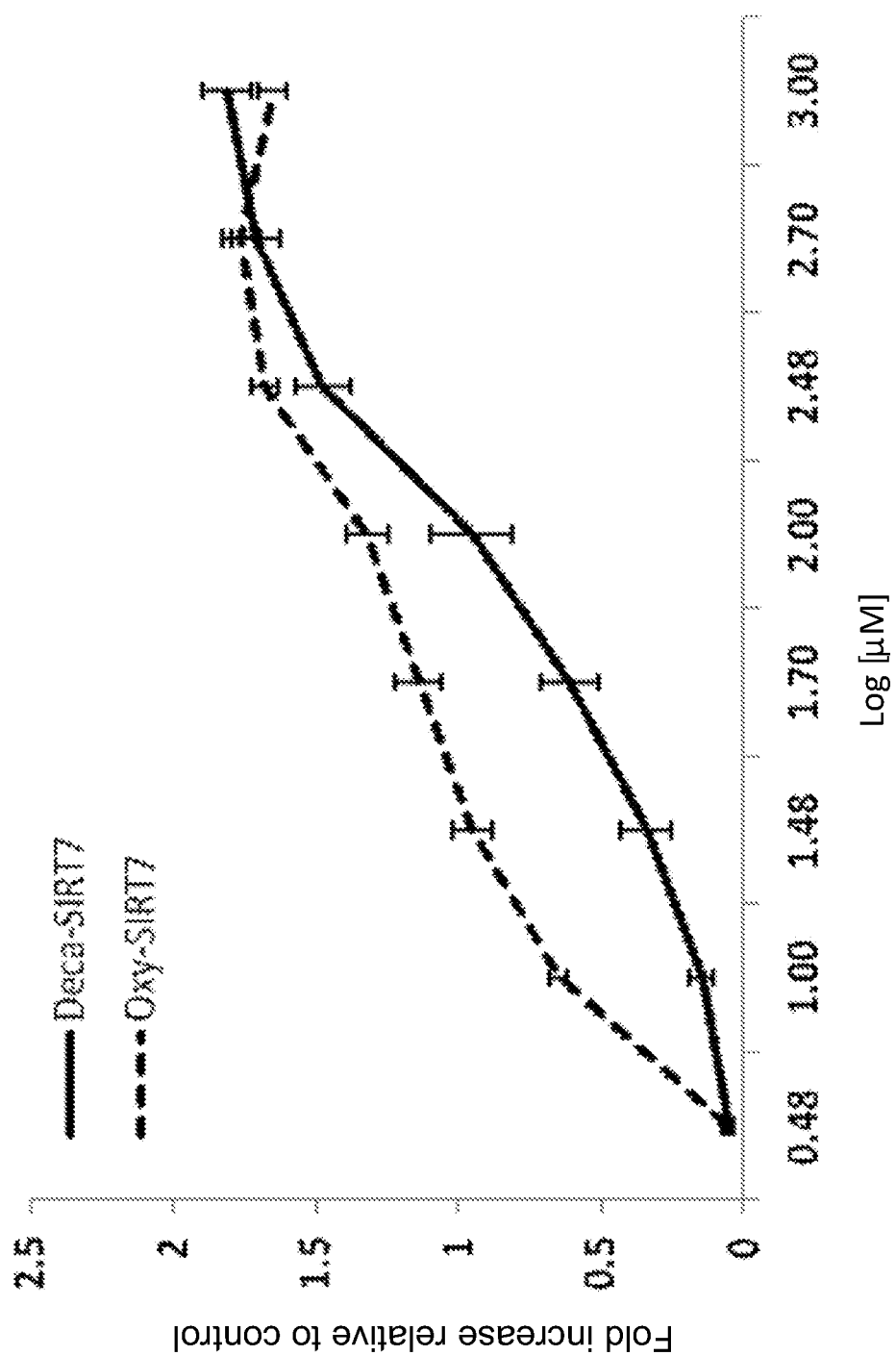
FIG. 1D shows dose-dependent transcriptional upregulation of SIRT7 (d). Data are expressed as fold increase relative to the internal control gene 18S, and represent means±SEM of 3 independent experiments.

Skin manifests the consequences of chronological and photoaging rendering us constantly aware of the aging process and seeking remedies to slow or reverse its impact. Skin aging has traditionally been categorized as extrinsic or intrinsic. Recent evidence indicates that both types share important molecular features including altered signal transduction pathways that promote matrix metalloproteinase expression, decreased procollagen synthesis, and connective tissue damage.

In human skin, aging is associated with an increased number of senescent cells and a reduced capacity for cellular proliferation and differentiation. Substantial evidence supports the theory that aging is predominantly a consequence of free radical damage by various endogenous reactive oxygen species (ROS). Velarde et al. reported on the in vivo evidence for a causal relationship between mitochondrial oxidative damage, cellular senescence, and aging phenotypes in the skin. Furthermore, ultraviolet (UV) radiation stimulates ROS synthesis, which has been implicated in mutagenesis and photoaging. In line with these findings, data suggest altered expression of sirtuin activity in UV irradiated versus sun-protected skin and that these differences may be responsible for certain aspects of skin aging.

Cellular senescence describes a process in which cells cease dividing and undergo distinctive phenotypic alterations, including profound chromatin and secretome changes, as well as tumor-suppressor activation. Numerous reports helped establish the concept of sirtuins as potent anti-aging proteins, detailing their pleiotropic roles in delaying cellular senescence and premature aging. Sirtuins are key effectors in pathways such as DNA damage repair, telomere shortening, the cellular response to oxidative stress, and ameliorating ROS-induced pathologies.

In mammals, there are seven sirtuin genes (SIRT1-7) localized in different cellular compartments and capable of diverse actions. Biochemically, sirtuins are a class of proteins that possesses mainly NAD+-dependent lysine deacetylase activity. Sirtuins are broadly recognized as critical regulators of multiple metabolic pathways, sensors of energy and redox status in cells, and modulators of oxidative stress.

These findings have triggered interest in developing small molecule activators or pharmaceuticals to help slow the progression of aging and its wide range of age-associated disorders. Of the seven mammalian sirtuins, SIRT1 has been the most extensively studied with regards to aging and longevity. For instance, the anti-aging effects of resveratrol are primarily attributed to SIRT1 activation. Indeed, Ido et al. reported that resveratrol, via increasing the activity of AMP-activated protein kinase and sirtuins, ameliorated cellular senescence and proliferative dysfunction.

We have previously reported the potent hypopigmenting efficacy of decapeptide-12 in human skin. Further clinical studies revealed an overall improvement in facial skin appearance in patients with dyschromia who were treated twice daily with topical cream containing 0.01 percent of decapeptide-12 for 8 weeks. These findings led us to hypothesize that decapeptide-12 may modulate sirtuin activity to improve overall skin appearance. To clarify this possibility, we assessed the effects of decapeptide-12 on sirtuin transcription in human epidermal progenitors.

Reports detail the pleiotropic roles sirtuins play in repressing premature aging, delaying cellular senescence, enhancing longevity, and ameliorating a wide range of aging disorders. Herein, we report our findings on the potent sirtuin activator, decapeptide-12, and compare its performance to the well documented oxyresveratrol. Treatment of human epidermal keratinocyte progenitors with 100 micromolar decapeptide-12 increased transcription of SIRT1 by 141±11 percent relative to control cells, whereas levels of SIRT3, SIRT6, and SIRT7 were increased by 121±13 percent, 147±8 percent, and 95±14 percent, respectively. Decapeptide-12 upregulated sirtuin transcription to similar levels as oxyresveratrol but with reduced cytotoxicity.

Materials and Methods

Reagents

Decapeptide-12 (YRSRKYSSWY) SEQ ID NO: 9 was synthesized by Bio Basic, Inc. (Ontario, Canada) using solid-phase FMOC chemistry. Oxyresveratrol was purchased from Sigma-Aldrich (St. Louis, MO).

Cell Culture

Human neonatal epidermal progenitors (Thermo Fisher Scientific, NY) were seeded in 6-well plates at a density of $2 \times 10^5$ cells per well. Each well received 2 milliliters of Epilife media containing 60 micromolar calcium chloride (Thermo Fisher Scientific, NY). Plates were incubated in a humidified chamber at 37 degrees Celsius and 5 percent $CO_2$. Twenty-four hours later, cells were treated with various concentrations of oxyresveratrol or decapeptide-12 dissolved in PBS containing 5 percent DMSO. Control wells received vehicle only (5 percent DMSO and PBS). Final concentration of DMSO in each well was 0.05 percent.

Total RNA Extraction, Quantitation, and cDNA Synthesis

After a 72 hour incubation period, cells were trypsinized and total RNA extracted, using RNeasy kit (Qiagen, Valencia, CA) according to the manufacturer's protocol.

RNA concentration was determined using nanodrop (Thermo fisher scientific, NY). Two µg of total RNA were used to synthesize cDNA using oligo dT primers and TaqMan reverse transcription reagents (Thermo fisher scientific, NY). The reaction was carried out in DNA Engine Peltier Thermal Cycler (Bio-Rad, Hercules, CA). The annealing temperature was 25 degrees Celsius for 10 minutes, followed by first strand synthesis at 48 degrees Celsius for 1 hour, and heat inactivation at 95 degrees Celsius for 5 minutes.

Semi-Quantitative Analysis

The SIRT1-7 primers (table A) were designed using Primer3. The semi-quantitative PCR reactions were performed on a DNA Engine Peltier Thermo Cycler (Bio-Rad, Hercules, CA). PCR was carried under the following conditions: denaturation at 94 degrees Celsius for 2 minutes and primer extension at 54 degrees Celsius for 30 seconds in 34 cycles for SIRT 1-7 and the housekeeping gene 18S.

TABLE A

Primer sequences for SIRT1-7 and 18S

| Gene | Primer sequence (5'-3') |
|---|---|
| SIRT1 SEQ ID NO: 1 | F GCCAATCATAAGATGTTGCTGAAC R TAGAGCCTCACATGCAAGCTCTA |
| SIRT2 SEQ ID NO: 2 | F AACCTCCCTCATCTCTAACT R GTCTCCAATAAGCAATGTCT |
| SIRT3 SEQ ID NO: 3 | F GTTGGTTACAAGATCCAGAC R AGATAGAAAGTGCTGGAATG |
| SIRT4 SEQ ID NO: 4 | F AGAGCTGTGAGAGAATGAAG R TTTCTGACCTGTAGTCTGGT |
| SIRT5 SEQ ID NO: 5 | F TCTTCCATACACTTTACTACCTT R TTTATATGATAGTGTCTTGTTGC |
| SIRT6 SEQ ID NO: 6 | F CAGCTTAAACAGGAGTGAAC R TTATTGCATTGAGGACTTTT |
| SIRT7 SEQ ID NO: 7 | F GACATTTTTAGCCATTTGTC R CATCCAGTACAGAGAGGATT |
| 18S SEQ ID NO: 8 | F CGGAGGTTCGAAGACGATCAGATA R TTGGTTTCCCGGAAGCTGCC |

Samples were run and resolved on a 1.5 percent agarose gel containing 0.5 micrograms per milliliters of ethidium bromide and imaged using the FluorChem HD2 Imaging System (Protein simple, San Jose, CA). Densitometry analysis was carried out using the AlphaEase FC software (Protein simple, San Jose, CA). Intensity ratios were calculated as the intensity value for each gene divided by the intensity value of the internal control gene 18S.

Viability/Proliferation and Cytotoxicity Assays

Proliferation rates were determined using a TACS® MTT Cell Proliferation Kit (R&D systems, Minneapolis, MN). Cells were seeded at $2.5 \times 10^4$ per well in 96-well plates in a humidified atmosphere with 5 percent $CO_2$ at 37 degrees Celsius. Twenty-four hours later, decapeptide-12 or oxyresveratrol were added to the corresponding wells at varying concentrations (0, 3, 10, 30, 100, 300, and 1000 micromolar), and cultures were then incubated for 72 hours. The remainder of the procedure was performed following the manufacturer's protocol.

Cellular toxicity was measured using a trypan blue dye exclusion assay. Cells were cultured in 6-well plates at a density of $4 \times 10^5$ cells per well. Each well received a different concentration of decapeptide-12 or oxyresveratrol (0, 3, 10, 30, 100, 300, and 1000 micromolar). Plates were incubated at 37 degrees Celsius in a humidified 5 percent $CO_2$ chamber. After 72 hours, an aliquot was taken and cells counted using a hemacytometer. Cytotoxicity was measured according to the following formula: [1−(# of cells in control−# of live cells in test sample)/# of cells in control]×100 percent.

cell death, respectively. At 1 millimolar, decapeptide-12 or oxyresveratrol resulted in 7±2 percent or 16±2 percent cell death, respectively.

Figure 2A:
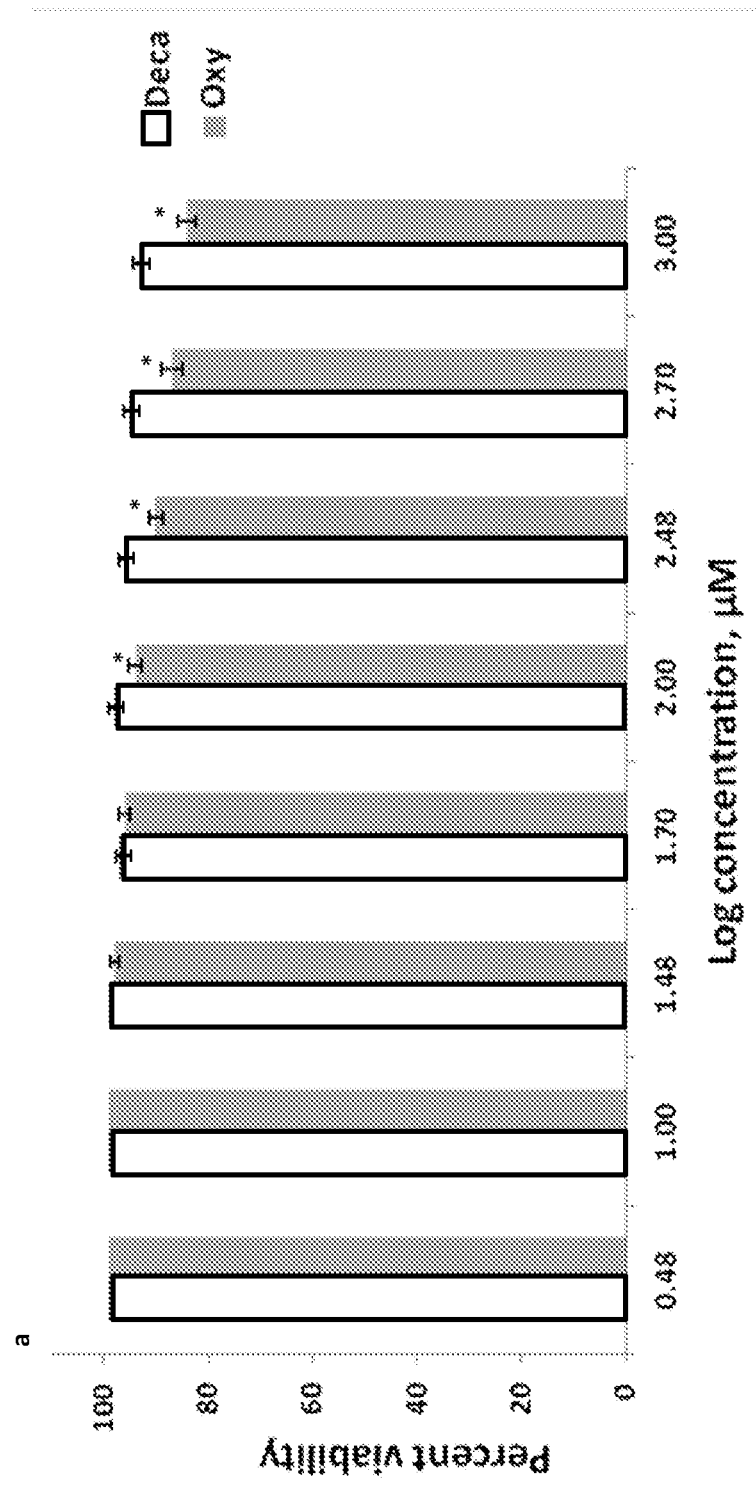
FIG. 2A shows cytotoxic effects of decapeptide-12 and oxyresveratrol on epidermal keratinocytes. Data are expressed as percent control and represent means±SEM of 3 separate experiments. *P<0.05.
Figure 2B:
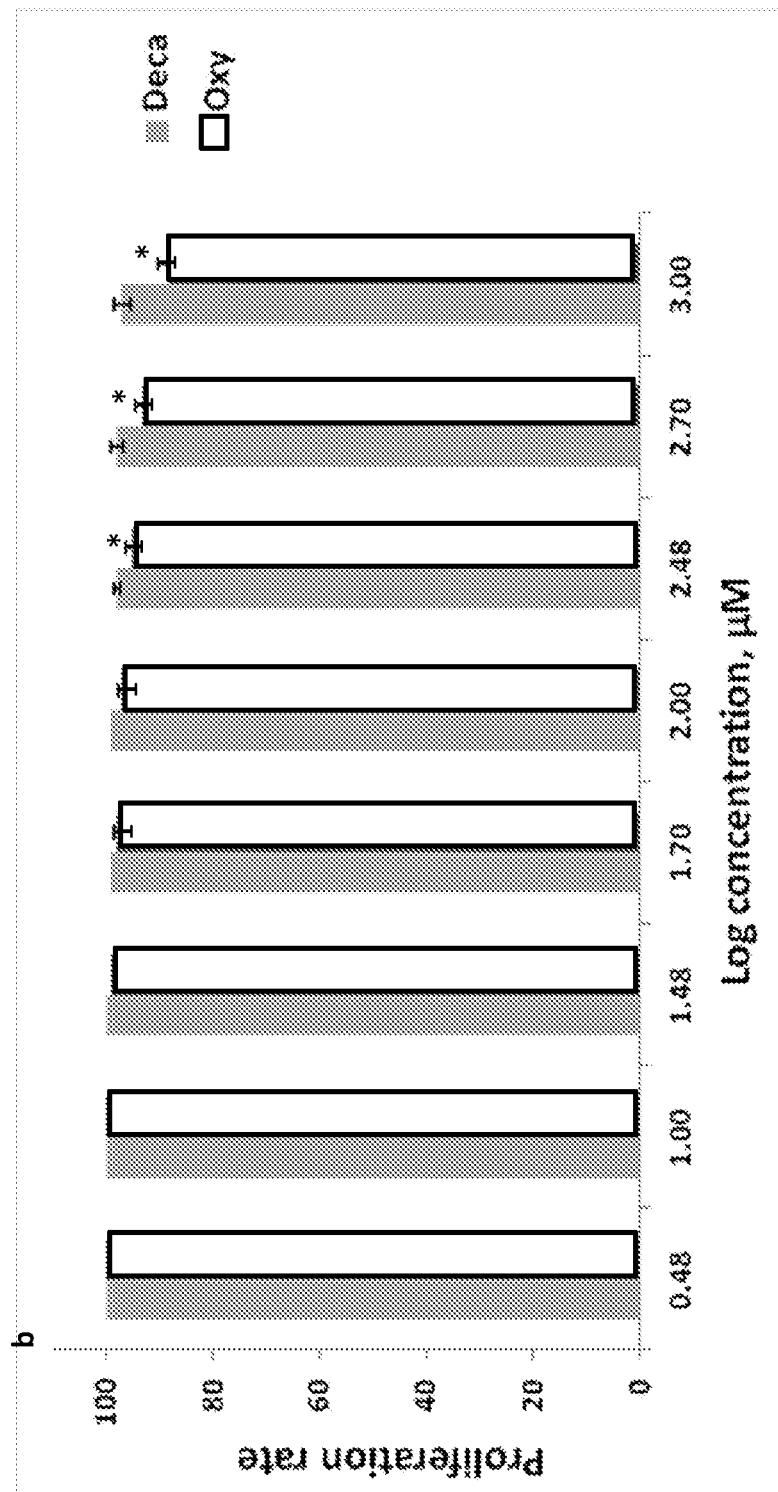
FIG. 2B shows effects of decapeptide-12 and oxyresveratrol on epidermal keratinocytes proliferation. Data are expressed as percent control and represent means±SEM of 3 separate experiments. *P<0.05.

We also evaluated the effects of decapeptide-12 and oxyresveratrol on the viability and proliferation of human epidermal progenitors. FIG. 2B shows that treatment with 300 micromolar decapeptide-12 or oxyresveratrol resulted in 2±1 percent or 5±1 percent reduced cell proliferation, respectively. However, unlike 1 millimolar decapeptide-12 which reduced proliferation 3±2 percent, 3-d incubation with oxyresveratrol reduced proliferation 12±2 percent.

Decapeptide-12 Upregulated Transcription of SIRT1-7:

We next assessed the effect of oxyresveratrol and decapeptide-12 on sirtuin expression in human epidermal progenitors. FIGS. 1A-1D and table B show decapeptide-12 and oxyresveratrol modulated transcription of SIRT1-7 in a dose-dependent fashion. At 30 micromolar oxyresveratrol, SIRT1 transcription levels were upregulated by 125±9 percent relative to control cells, whereas SIRT3, SIRT6, and SIRT7 were upregulated by 133±5 percent, 73±8 percent, and 95±7 percent, respectively.

Table B and Table C. Gene expression profile of SIRT 1-7 in response to treatment with decapeptide-12 (table B) and oxyresveratrol (table C). Results are averages of three independent runs.

TABLE B

| Deca [μM] | SIRT1 | SIRT2 | SIRT3 | SIRT4 | SIRT5 | SIRT6 | SIRT7 |
| --- | --- | --- | --- | --- | --- | --- | --- |
| 3 | 3 ± 1% | 1 ± 1% | 4 ± 1% | 3 ± 1% | 3 ± 1% | 3 ± 1% | 5 ± 1% |
| 10 | 12.2 ± 3.1% | 4.1 ± 3% | 9.2 ± 2.8% | 8.1 ± 4% | 5.2 ± 3% | 21.3 ± 8.1% | 15 ± 4.2% |
| 30 | 34 ± 6.7% | 11.2 ± 3.7% | 32.2 ± 6.1% | 12.1 ± 7% | 21 ± 6.7% | 52 ± 5.1% | 34.4 ± 9.2% |
| 50 | 79.2 ± 12% | 21.5 ± 4.9% | 65 ± 12.1% | 41.2 ± 13.1% | 33.1 ± 6.1% | 95.4 ± 13.4% | 61.3 ± 10.2% |
| 100 | 141.2 ± 11% | 35.4 ± 5.5% | 121 ± 13.2% | 71.4 ± 14.1% | 46 ± 7.3% | 147 ± 8.4% | 95.4 ± 14.2% |
| 300 | 188 ± 12% | 61.1 ± 6.8% | 165.2 ± 12.4% | 115 ± 11.7% | 67 ± 9.3% | 189 ± 9.5% | 148 ± 9.6% |
| 500 | 205 ± 13.3% | 76 ± 6.1% | 177 ± 9.2% | 145 ± 12.7% | 87.4 ± 15.1% | 194 ± 14% | 171.4 ± 8.4% |
| 1000 | 213 ± 13.4% | 76 ± 7.1% | 171 ± 9% | 151 ± 13.4% | 92.1 ± 16.8% | 167 ± 12.2% | 181.1 ± 8.4% |

TABLE C

| Oxy [μM] | SIRT1 | SIRT2 | SIRT3 | SIRT4 | SIRT5 | SIRT6 | SIRT7 |
| --- | --- | --- | --- | --- | --- | --- | --- |
| 3 | 8.7 ± 1% | 7.9 ± 2% | 10 ± 3% | 8.1 ± 1% | 7.1 ± 1% | 6.1 ± 1% | 6.3 ± 1% |
| 10 | 45 ± 7.7% | 14.9 ± 1.9% | 52.7 ± 5.1% | 12.4 ± 2.1% | 12.3 ± 3% | 34 ± 5.5% | 65 ± 2.9% |
| 30 | 124.5 ± 8.6% | 43.1 ± 2.4% | 133 ± 4.8% | 49 ± 6.7% | 45.1 ± 4.3% | 73 ± 8.1% | 95 ± 6.7% |
| 50 | 166 ± 14.5% | 56.3 ± 7.7% | 156 ± 9.2% | 52.1 ± 6.6% | 46 ± 4% | 81.3 ± 8.1% | 114 ± 8.1% |
| 100 | 187 ± 16.6% | 41.2 ± 8.1% | 148 ± 7.3% | 64.1 ± 7.4% | 36.1 ± 6.7% | 82.4 ± 8.4% | 132 ± 7.6% |
| 300 | 187 ± 15.4% | 39 ± 9.3% | 152.2 ± 9% | 67 ± 8.7% | 33.4 ± 7.1% | 87.4 ± 9.3% | 168 ± 4.8% |
| 500 | 176 ± 10% | 33.1 ± 12.4% | 151 ± 8.1% | 61.2 ± 8.8% | 35.1 ± 8.1% | 81.2 ± 12.4% | 177 ± 6.6% |
| 1000 | 175 ± 9% | 31.2 ± 12.3% | 151 ± 7.4% | 71.3 ± 9.2% | 37 ± 6.8% | 75 ± 15.1% | 165 ± 5.1% |

Statistical Analysis

The means and their standard errors were calculated from 3 independent runs using Microsoft Excel, and statistical significance was determined using a paired analysis of variance. P values were taken to be statistically significant at $P<0.05$.

Results

Effects of Decapeptide on Proliferation Rates and Cytotoxicity:

We first assessed the cytotoxic effect of decapeptide-12 and oxyresveratrol on human epidermal progenitors. FIG. 2A shows that treatment with 100 micromolar decapeptide-12 or oxyresveratrol resulted in 3±1 percent or 6±1 percent The data shows that 100 micromolar decapeptide-12 increased transcription of SIRT1 by 141±11 percent relative to untreated cells, whereas SIRT3, SIRT6 and SIRT7 increased by 121±13 percent, 147±8 percent, and 95±14 percent, respectively (FIGS. 1A-1D).

Discussion

The pleiotropic roles sirtuins play in delaying cellular senescence and blocking the development of premature aging has helped substantiate them as potent anti-aging proteins. Therapeutic use of resveratrol as a SIRT1 activator and potential anti-aging agent has been extensively researched and documented. Resveratrol protects human endothelium from H2O2-induced oxidative stress and senescence via SIRT1 activation. Similarly, oxyresveratrol is also a potent antioxidant and free radical scavenger. However, unlike resveratrol, it exhibits less cytotoxicity and better water solubility. Consequently, we elected to use it as a positive control against which we compared decapeptide-12's performance and ability to modulate sirtuin transcription in human epidermal keratinocytes.

Even though all 7 sirtuins were upregulated after treatment with decapeptide-12, our discussion will focus on those sirtuins directly implicated in skin aging.

At 100 micromolar or 1 millimolar, decapeptide-12 increased SIRT1 transcription by an impressive 141 or 213 percent, respectively. SIRT1 is primarily a nuclear deacetylase. It controls various cellular processes such as cell proliferation, differentiation, apoptosis, metabolism, stress response, genome stability, and cell survival. Cao et al reported that SIRT1 confers protection against UVB- and H2O2-induced cell death via modulation of p53 and c-Jun N-terminal kinases in cultured skin keratinocytes, suggesting that SIRT1 activators could serve as new anti-skin aging agents. Other researchers reported that SIRT1 can suppress NF-κB signaling and thus delay the aging process and extend lifespan. SIRT1 activation inhibits NF-κB signaling directly by deacetylating the p65 subunit of NF-κB complex and enhances oxidative metabolism and the resolution of inflammation. Consequently, SIRT1 can be regarded as a crucial anti-aging protein which mediates its widespread effects in preventing premature senescence and accelerated aging by regulating multiple molecular pathways.

SIRT3 transcription was increased by 121 percent following treatment with 100 micromolar decapeptide. SIRT3 has been primarily linked to the regulation of a variety of mitochondrial processes, such as β-oxidation, ATP generation, and management of ROS. SIRT3 has also been implicated in the maintenance of regenerative capacity of hematopoietic stem cells. SIRT3 is suppressed with aging, and SIRT3 upregulation in aged hematopoietic stem cells improves their regenerative capacity. This discovery establishes the significant role SIRT3 plays in maintaining stemness, and more importantly, helps lay the path for future stem cell-based interventions for metabolic disorders resulting in premature aging.

SIRT6 can be regarded as an important anti-aging protein with multifaceted roles in DNA damage repair, metabolic regulation, inflammation, and tumor suppression. SIRT6 gained prominence when its knockout mouse model developed severe premature aging phenotypes with mortality resulting within a month. Moreover, SIRT6 is the only mammalian sirtuin which displayed clear increase in lifespan when overexpressed in the whole body of mice. Furthermore, Kawahara et al. reported that SIRT6 attenuates hyperactive NF-κB signaling by deacetylating histone H3 at K9 on the promoters of NF-κB target genes, which enhances the role of SIRT6 as a critical anti-inflammatory protein.

Baohua et al. showed that SIRT6 plays a key role in the process of skin aging via modulation of collagen metabolism and NF-κB signaling. They reported that blocking SIRT6 significantly decreased hydroxyproline content by inhibiting transcription of type 1 collagen, prompting matrix metalloproteinase1 secretion and increasing NF-κB signaling. Taken together, SIRT6 stands out as a key modulator of anti-aging processes, by regulating multiple pathways to delay cellular senescence and accelerated aging. Hence, decapeptide-12, which enhanced SIRT6 transcription by 147 percent at 100 μM, may hold great promise as a therapeutic anti-aging candidate to address the often concurrent phenotypes of premature skin aging and photodamaged skin.

In summary, decapeptide-12 was shown in this report to significantly upregulate transcription levels of SIRT1, SIRT3, and SIRT6, all 3 of which play significant roles in counteracting skin aging and other age-associated pathologies. Clinical studies with various topical formulations containing decapeptide-12 are currently being designed to help validate the in vitro findings and test the efficacy of this potent sirtuin activator in vivo.

EXAMPLE

In this example, certain modifications to the P4 decapeptide were made, as detailed in the following table D.

TABLE D

| Peptide | Short Ref. | Sequence | Modification |
| --- | --- | --- | --- |
| Native-P4<br>SEQ ID NO: 9 | P4 | YRSRKYSSWY | None |
| Palm-P4-Amid<br>SEQ ID NO: 10 | P4A | Palmitoyl-YRSRKYSSWY-amide | •N-terminal: Palmitoyl.<br>•C-terminal: Amide. |
| Palm-D-ISO-Amid<br>SEQ ID NO: 11 | P4B | Palmitoyl-YRSRK[*Y]SSWY-amide | •N-terminal: Palmitoyl.<br>•Internal: Tyrosine at position 6 in the D-Isoform.<br>•C-terminal: Amide. |
| Accet-P4-Amid<br>SEQ ID NO: 12 | P4C | Acetyl-YRSRKYSSWY-amide | •N-Terminal: Acetyl.<br>•C-terminal: Amide. |

These modifications to decapeptide P4 may serve to improve stability against proteases and to enhance transcutaneous or transcellular penetration, or both.

Peptides of the present invention may comprise residues from any of the naturally occurring amino acids, or from nonnaturally occurring amino acids. These naturally occurring and nonnaturally-occurring amino acids may be in the D or L configuration, or may include both dextrorotary forms. The terms D and L are used in this application as they are known to be used in the art. Peptides of the invention include single amino acids and short spans (e.g., 1-20) of amino acids. In addition, modified peptides of the present invention may also include a monomer or dimer.

The standard single letter and three letter codes for amino acids are used in this application and are in table E below.

TABLE E

| | | |
|---|---|---|
| A (Ala) Alanine | C (Cys) Cysteine | D (Asp) Aspartic acid |
| E (Glu) Glutamic acid | F (Phe) Phenylalanine | G (Gly) Glycine |
| H (His) Histidine | I (Ile) Isoleucine | K (Lys) Lysine |
| L (Leu) Leucine | M (Met) Methionine | N (Asn) Asparagine |
| P (Pro) Proline | Q (Gln) Glutamine | R (Arg) Arginine |
| S (Ser) Serine | T (Thr) Threonine | V (Val) Valine |
| W (Trp) Tryptophan | Y (Tyr) Tyrosine | |

As described above, the indicated residues may be the naturally occurring L amino acid, or a modification of these, that is, a chemical modification, an optical isomer, or a link to a modifying group. It is contemplated that specific modifications may be made within the peptide that maintain the ability of the present peptides to specifically modulate the expression of sirtuin gene(s).

The effect of the decapeptides P4, P4A, P4B, and P4C upon the transcription levels of sirtuins 1-7 was evaluated. Table F summarizes transcription levels for all four decapeptides with the corresponding genes, at tested concentrations of: 10, 30, 50, 100, and 300 (all in micromolar).

TABLE F

| Concentration | Gene | P4 | P4A | P4B | P4C |
|---|---|---|---|---|---|
| 10 µM | SIRT1 | 12 ± 3% | 18 ± 2% | 10 ± 4% | 7 ± 3% |
| | SIRT2 | 4 ± 3% | 14 ± 1% | 5 ± 1% | 5.00 |
| | SIRT3 | 9 ± 3% | 25 ± 4% | 22 ± 3% | 8 ± 3% |
| | SIRT4 | 8 ± 3% | 16 ± 1% | 9 ± 1% | 3 ± 1% |
| | SIRT5 | 5 ± 3% | 13 ± 2% | 2.00 | 4 ± 1% |
| | SIRT6 | 21 ± 8% | 24 ± 5% | 21 ± 5% | 12 ± 3% |
| | SIRT7 | 15 ± 4% | 29 ± 6% | 20 ± 6% | 14 ± 5% |
| 30 µM | SIRT1 | 34 ± 7% | 19 ± 1% | 10 ± 3% | 5.00 |
| | SIRT2 | 11 ± 4% | 15 ± 1% | 8 ± 3% | 2 ± 1% |
| | SIRT3 | 32 ± 6% | 26 ± 3% | 23 ± 2% | 6 ± 2% |
| | SIRT4 | 12 ± 7% | 16 ± 1% | 10 ± 1% | 3 ± 1% |
| | SIRT5 | 21 ± 7% | 12 ± 2% | 1.00 | 2 ± 1% |
| | SIRT6 | 52 ± 5% | 25 ± 5% | 22 ± 4% | 9 ± 4% |
| | SIRT7 | 34 ± 9% | 33 ± 5% | 23 ± 5% | 7 ± 2% |
| 50 µM | SIRT1 | 79 ± 12% | 42 ± 5% | 48 ± 3% | 1.00 |
| | SIRT2 | 22 ± 5% | 6 ± 3% | 17 ± 6% | 1.00 |
| | SIRT3 | 65 ± 12% | 60 ± 4% | 28 ± 5% | 45 ± 9% |
| | SIRT4 | 41 ± 13% | 9 ± 4% | 17 ± 1% | 11 ± 6% |
| | SIRT5 | 33 ± 6% | 10 ± 3% | 1.00 | 3 ± 1% |
| | SIRT6 | 95 ± 13% | 33 ± 7% | 10 ± 4% | 31 ± 5% |
| | SIRT7 | 61 ± 10% | 52 ± 4% | 54 ± 7% | 46 ± 5% |
| 100 µM | SIRT1 | 141 ± 11% | 144 ± 5% | 135 ± 12% | 137 ± 8% |
| | SIRT2 | 35 ± 5% | 48 ± 1% | 52 ± 4% | 42 ± 1% |
| | SIRT3 | 121 ± 13% | 152 ± 2% | 78 ± 10% | 82 ± 8% |
| | SIRT4 | 71 ± 14% | 98 ± 12% | 86 ± 6% | 32 ± 9% |
| | SIRT5 | 46 ± 7% | 47 ± 7% | 35 ± 3% | 35 ± 2% |
| | SIRT6 | 147 ± 8% | 135 ± 10% | 107 ± 2% | 124 ± 7% |
| | SIRT7 | 95 ± 14% | 87 ± 6% | 61 ± 7% | 80 ± 11% |
| 300 µM | SIRT1 | 188 ± 12% | 184 ± 2% | 155 ± 3% | 190 ± 9% |
| | SIRT2 | 61 ± 7% | 30 ± 5% | 40 ± 4% | 31 ± 9% |
| | SIRT3 | 165 ± 12% | 147 ± 2% | 142 ± 5% | 159 ± 6% |
| | SIRT4 | 115 ± 12% | 65 ± 1% | 49 ± 4 | 67 ± 9% |
| | SIRT5 | 67 ± 9% | 29 ± 4% | 29 ± 5% | 28 ± 9% |
| | SIRT6 | 189 ± 10% | 85 ± 5% | 81 ± 4% | 87 ± 3% |
| | SIRT7 | 148 ± 10% | 113 ± 2% | 103 ± 8% | 130 ± 9% |

At low concentrations, the native decapeptide P4 exhibited enhanced transcription levels relative to the modified decapeptides. However, each of the three of the modified decapeptides (P4A, P4B, and P4C) upregulated the transcription levels of the sirtuin genes relative to the control. At a concentration of 100 micromolar, the effect upon transcription level was comparable across all four decapeptides.

Proliferation rates for three human cell lines (epidermal progenitors, melanoblasts, and fibroblasts) were determined using a TACS® MTT Cell Proliferation Kit. Cells were seeded at 2.5×104 per well in 96-well plates in a humidified atmosphere with 5 percent $CO_2$ at 37 degrees Celsius. Twenty-four hours later, the decapeptides were added to the corresponding wells at varying concentrations and incubated for 72 hours. The remainder of the procedure was performed following the manufacturer's protocol.

Table G shows epidermal progenitor proliferation rate after 72 hours.

TABLE G

| Concentration (µM) | P4 | P4A | P4B | P4C |
|---|---|---|---|---|
| 3 | 100% | 99 ± 1% | 99 ± 1% | 99 ± 1% |
| 10 | 99 ± 1% | 99 ± 1% | 99 ± 1% | 99 ± 1% |
| 30 | 98 ± 1% | 98 ± 1% | 98 ± 1% | 98 ± 1% |
| 50 | 97 ± 1% | 97 ± 1% | 98 ± 1% | 98 ± 1% |
| 100 | 97 ± 1% | 97 ± 2% | 97 ± 1% | 97 ± 1% |
| 300 | 96 ± 1% | 96 ± 2% | 97 ± 1% | 97 ± 1% |
| 500 | 96 ± 2% | 96 ± 2% | 95 ± 2% | 96 ± 2% |
| 1000 | 94 ± 2% | 94 ± 2% | 94 ± 2% | 96 ± 2% |

Table H shows melanoblast proliferation rate after 72 hours.

TABLE H

| Concentration (µM) | P4 | P4A | P4B | P4C |
|---|---|---|---|---|
| 3 | 100% | 100% | 100% | 100% |
| 10 | 100% | 100% | 100% | 100% |
| 30 | 99 ± 1% | 99 ± 1% | 99 ± 1% | 99 ± 1% |
| 50 | 98 ± 1% | 98 ± 1% | 98 ± 1% | 98 ± 1% |
| 100 | 97 ± 1% | 97 ± 2% | 97 ± 2% | 97 ± 2% |

TABLE H-continued

| Concentration (μM) | P4 | P4A | P4B | P4C |
|---|---|---|---|---|
| 300 | 97 ± 1% | 97 ± 2% | 96 ± 2% | 96 ± 3% |
| 500 | 95 ± 2% | 96 ± 2% | 95 ± 2% | 95 ± 2% |
| 1000 | 95 ± 2% | 95 ± 2% | 94 ± 2% | 95 ± 2% |

Table I shows fibroblast proliferation rate after 72 hours.

TABLE I

| Concentration (μM) | P4 | P4A | P4B | P4C |
|---|---|---|---|---|
| 3 | 100% | 100% | 100% | 100% |
| 10 | 99 ± 1% | 99 ± 1% | 99 ± 1% | 99 ± 1% |
| 30 | 99 ± 1% | 98 ± 1% | 99 ± 1% | 99 ± 1% |
| 50 | 98 ± 1% | 98 ± 1% | 99 ± 1% | 99 ± 1% |
| 100 | 97 ± 1% | 97 ± 2% | 98 ± 2% | 98 ± 2% |
| 300 | 97 ± 1% | 97 ± 2% | 97 ± 2% | 97 ± 2% |
| 500 | 97 ± 2% | 96 ± 2% | 96 ± 2% | 96 ± 2% |
| 1000 | 96 ± 2% | 95 ± 2% | 96 ± 2% | 96 ± 2% |

After a 72-hour incubation of epidermal progenitors, melanoblasts, and fibroblasts with 100 micromolar of decapeptide P4A, the result was a 3 percent reduction in the proliferation rate of all three cell lines.

At 1000 micromolar, the proliferation rate of epidermal progenitors was reduced by 6 percent, whereas that of melanoblasts and fibroblasts was reduced by 5 percent and 4 percent, respectively.

The effect of each of the decapeptides upon cell viability was also tested. In particular, cells were incubated with the decapeptide at various concentrations and then counted for viability relative to the control (untreated cells) using trypan blue. Cytotoxicity was measured according to the following formula:

[1−(# of cells in control−# of live cells in test sample)/# of cells in control]×100 percent.

Table J shows epidermal progenitor viability after 7 days.

TABLE J

| Concentration (μM) | P4 | P4A | P4B | P4C |
|---|---|---|---|---|
| 3 | 100% | 100% | 100% | 100% |
| 10 | 99 ± 1% | 99 ± 1% | 99 ± 1% | 99 ± 1% |
| 30 | 98.4 ± 1% | 98.2 ± 1% | 98.2 ± 1% | 98 ± 1% |
| 50 | 97.8 ± 1% | 97.5 ± 1% | 98 ± 1% | 97.4 ± 1% |
| 100 | 97.1 ± 1% | 96.9 ± 2% | 97 ± 1% | 96.6 ± 2% |
| 300 | 95.6 ± 2% | 95.6 ± 2% | 96.5 ± 2% | 95.7 ± 3% |
| 500 | 94.2 ± 2% | 94.3 ± 2% | 95.5 ± 2% | 94.8 ± 3% |
| 1000 | 93.8 ± 2% | 93.6 ± 3% | 94.5 ± 2% | 94 ± 3% |

Table K shows melanoblast viability after 7 days.

TABLE K

| Concentration (μM) | P4 | P4A | P4B | P4C |
|---|---|---|---|---|
| 3 | 100% | 100% | 100% | 100% |
| 10 | 99 ± 1% | 99 ± 1% | 98.5 ± 1% | 99 ± 1% |
| 30 | 98.3 ± 1% | 98.5 ± 1% | 97.8 ± 3% | 98.4 ± 1% |
| 50 | 98 ± 1% | 98 ± 1% | 97.2 ± 2% | 97.9 ± 1% |
| 100 | 97.3 ± 1% | 97 ± 2% | 96.3 ± 2% | 97 ± 2% |
| 300 | 95.2 ± 2% | 96.2 ± 2% | 95.6 ± 2% | 96 ± 3% |
| 500 | 94.6 ± 2% | 95.6 ± 2% | 94.6 ± 2% | 95.5 ± 3% |
| 1000 | 94 ± 2% | 94.8 ± 2% | 93.8 ± 2% | 94.8 ± 3% |

Table L shows fibroblast viability after 7 days.

TABLE L

| Concentration (μM) | P4 | P4A | P4B | P4C |
|---|---|---|---|---|
| 3 | 100% | 100% | 100% | 100% |
| 10 | 98.6 ± 1% | 98.9 ± 1% | 98.8 ± 1% | 98.9 ± 1% |
| 30 | 98.2 ± 1% | 98.4 ± 1% | 98.3 ± 1% | 98.3 ± 1% |
| 50 | 97.8 ± 1% | 98 ± 1% | 97.6 ± 1% | 97.8 ± 1% |
| 100 | 97.2 ± 1% | 97.4 ± 2% | 97.3 ± 2% | 97.4 ± 2% |
| 300 | 95.6 ± 2% | 96.6 ± 2% | 96.5 ± 2% | 96.5 ± 2% |
| 500 | 94.5 ± 2% | 95.5 ± 2% | 95.3 ± 3% | 95.7 ± 2% |
| 1000 | 93.8 ± 1% | 94.3 ± 2% | 94.2 ± 3% | 94.9 ± 3% |

At the 100 micromolar concentration, cell viability remained over 97 percent for all three cell lines. At 1000 micromolar, cell viability dropped by 6 percent relative to the control.

In conclusion, recent reports detail the pleiotropic roles sirtuins play in repressing premature aging, delaying cellular senescence, enhancing longevity, and ameliorating a wide range of aging disorders. Herein, we report our findings on the potent sirtuin activator, decapeptide-12, and compare its performance to the well documented oxyresveratrol. Treatment of human epidermal progenitors with 100 micromolar decapeptide-12 increased transcription of SIRT1 by 141±11 percent relative to control cells, whereas levels of SIRT3, SIRT6, and SIRT7 were increased by 121±13 percent, 147±8 percent, and 95.4±14 percent, respectively. Decapeptide-12 upregulated sirtuin transcription to similar levels as oxyresveratrol but with reduced cytotoxicity. Thus, decapeptide-12 may hold promise as a safer therapeutic to counteract skin aging and other age-associated pathologies.

While the above description mentions a typical decapeptide concentration of 100 micromolar or greater in noting where the effect was evident, the results also demonstrate lower concentrations as having a positive effect. Thus some embodiments may utilize a decapeptide concentration of 1 micromolar or greater, with particular embodiments employing a peptide concentration range of 100 micromolar or greater. Examples of peptide concentration ranges according to various embodiments are 1 micromolar or greater, 5 micromolar or greater, 10 micromolar or greater, 30 micromolar or greater, 50 micromolar or greater, 100 micromolar or greater, 300 micromolar or greater, 500 micromolar or greater, and 1000 micromolar or greater.

It is further noted that a particular decapeptide may be used in combination with other component(s) in order to achieve the desired effect. For example, a particular decapeptide could be used in combination with other peptides such as decapeptides P4A, 4B, and/or 4C and/or with other components such as oxyresveratrol. According to such embodiments, a synergistic effect realized by including other components may ultimately reduce the concentration of any individual component (e.g., decapeptide, other) that is needed to achieve the desired result.

While the above specifically includes decapeptides and oxyresveratrol as possible additional components, embodiments are not limited to this. Examples of other possible additives can include but are not limited to, α-lipoic acid, biotin, caffeine, ceramides, coenzyme Q10, glycolic acid, green tea, human stem cells, human stem cell extracts, hyaluronic acid, hydroquinone, jojoba oil, kojic acid, lactic acid, malic acid, niacinamide, oligopeptides, peptides, plant stem cells, plant stem cell extracts, resveratrol, retinol, vitamin C, vitamin E, and vitamin K, amongst others.

It is noted that embodiments may be utilized to treat a variety of skin cell types. Examples of terminally differentiated skin cells can include but are not limited to keratinocytes, fibrocytes, melanocytes, and immune cells such as langerhans cells (e.g., histiocyte or dendrocytes) that age over time as well.

Embodiments may also be utilized to treat skin progenitor cells to reduce skin aging and allow for skin renewal over its lifetime. Examples of such progenitor cells may include but are not limited to epidermal keratinocyte progenitors, fibroblasts, melanoblasts, histioblasts, or dendroblasts which are progenitors for langerhans cells that lodge in the epidermis.

Finally, while the above has described the treatment of human skin cells, specific embodiments are not limited to such approaches. Alternative embodiments could employ the treatment of skin cells from other organisms, including but not limited to mammals such as cows (e.g., in the manufacture of leather), pigs, and other animals (e.g., dogs, cats, and others that may be valued based upon skin appearance for contest purposes).

Clause 1A. A peptide consisting of SEQ ID NO: 9, SEQ ID NO: 10, SEQ ID NO: 11, or SEQ. ID NO: 12.

Clause 2A. The peptide of clause 1A wherein the peptide consists of SEQ ID NO: 9 modified by a modifying group, the modifying group being either a palmitoyl group or an acetyl group at an amino-terminal end, or amidation of a carboxy-terminal end, or both.

Clause 3A. The peptide according to any of clauses 1A-2A consisting of SEQ ID NO: 11 having a tyrosine amino acid at a position 6 as a D-isoform, and all other amino acids being L-isoforms.

Clause 4A. A composition comprising a first peptide consisting of SEQ ID NO: 9, SEQ ID NO: 10, SEQ ID NO: 11, or SEQ. ID NO: 12.

Clause 5A. The composition of clause 4A wherein the peptide consists of SEQ ID NO: 9 modified by a modifying group, the modifying group being either a palmitoyl group or an acetyl group at an amino-terminal end, or amidation of a carboxy-terminal end, or both.

Clause 6A. The composition according to any of clauses 4A-5A consisting of SEQ ID NO: 11 having a tyrosine amino acid at a position 6 as a D-isoform, and all other amino acids being L-isoforms.

Clause 7A. The composition according to any of clauses 4A-6A wherein the peptide is present in a concentration of 1 µm or greater.

Clause 8A. A method of treating a subject by modulating expression of a sirtuin gene in a skin cell to reduce symptoms of skin aging, the method comprising administering to a subject in need thereof a composition comprising an effective amount of one or more peptides, wherein the one or more peptides consist of, SEQ ID NO: 9, SEQ ID NO: 10, SEQ ID NO: 11, or SEQ. ID NO: 12.

Clause 9A. The method according to clause 8A wherein the peptide consists of SEQ ID NO: 9 modified by a modifying group, the modifying group being either a palmitoyl group or an acetyl group at an amino-terminal end, or amidation of a carboxy-terminal end, or both.

Clause 10A. The method according to any of clauses 8A-9A wherein the peptide consists of SEQ ID NO: 11 having a tyrosine amino acid at a position 6 as a D-isoform, and all other amino acids being L-isoforms.

Clause 11A. The method according to any of clauses 8A-10A wherein the skin cell is a progenitor.

Clause 12A. The method according to clause 11A wherein the progenitor is an epidermal keratinocyte progenitor, a melanoblast, a fibroblast, a histioblast, or a dendroblast.

Clause 13A. The method according to any of clauses 8A-10A wherein the skin cell is terminally differentiated.

Clause 14A. The method according to clause 13A wherein the skin cell is a keratinocyte, a melanocyte, a fibrocyte, a histiocyte, or a dendrocyte.

Clause 15A. The method according to any of clauses 8A-14A wherein the peptide is present in a concentration of 1 µm or greater.

Clause 16A. The method of according to any of clauses 8A-15A wherein the sirtuin gene comprises SEQ ID NO: 1, SEQ ID NO: 2, SEQ ID NO: 3, SEQ ID NO: 4, SEQ ID NO: 5, SEQ ID NO: 6, or SEQ ID NO: 7.

Clause 17A. The method according to any of clauses 8A-16A wherein the composition further comprises oxyresveratrol.

Clause 18A. The method according to any of clauses 8A-17A wherein the skin cell is a mammal cell.

Clause 19A. The method according to clause 18A wherein the skin cell is human.

Clause 20. A method of modulating expression of a sirtuin gene in a skin cell, the method comprising administering to a subject in need thereof a composition comprising an effective amount of one or more peptides, wherein the one or more peptides consist of, SEQ ID NO: 9, SEQ ID NO: 10, SEQ ID NO: 11, or SEQ. ID NO: 12.

Figure 3:
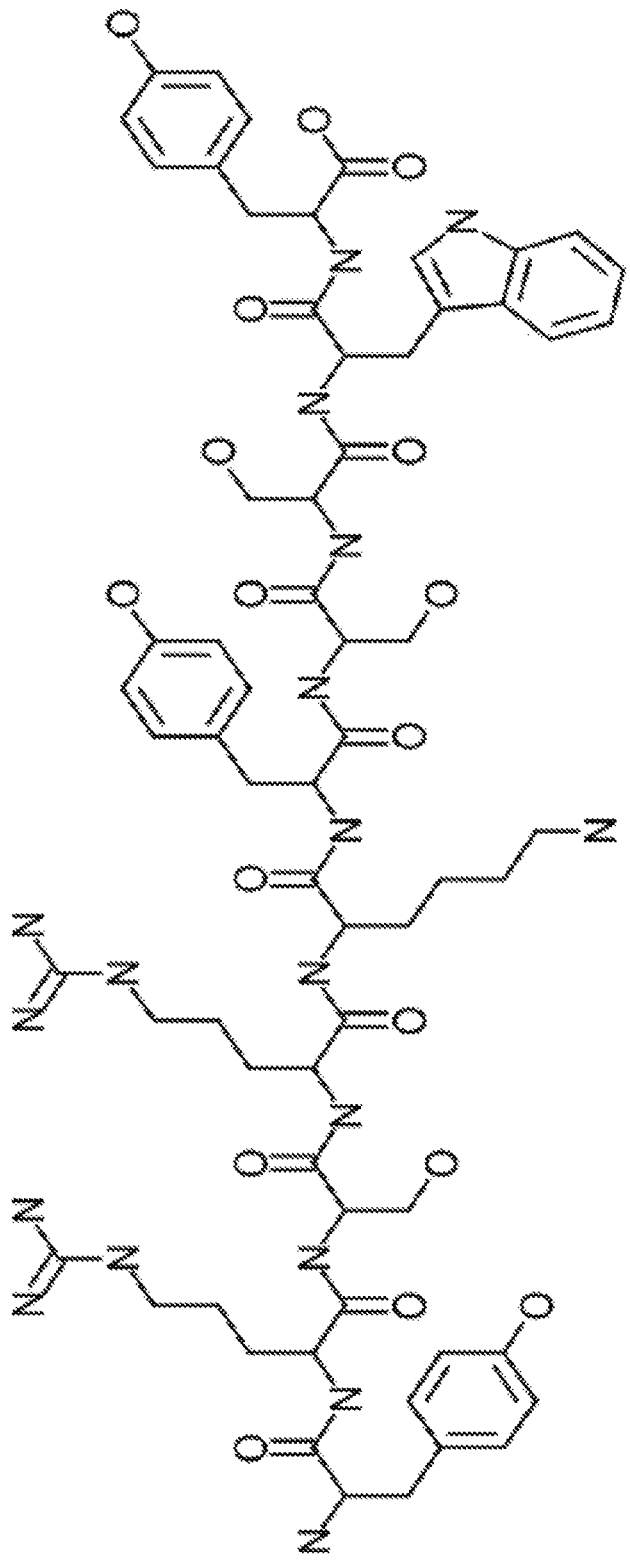
FIG. 3 shows the chemical structure of the decapeptide P4 of the SEQ ID NO: 9.
Figure 4:
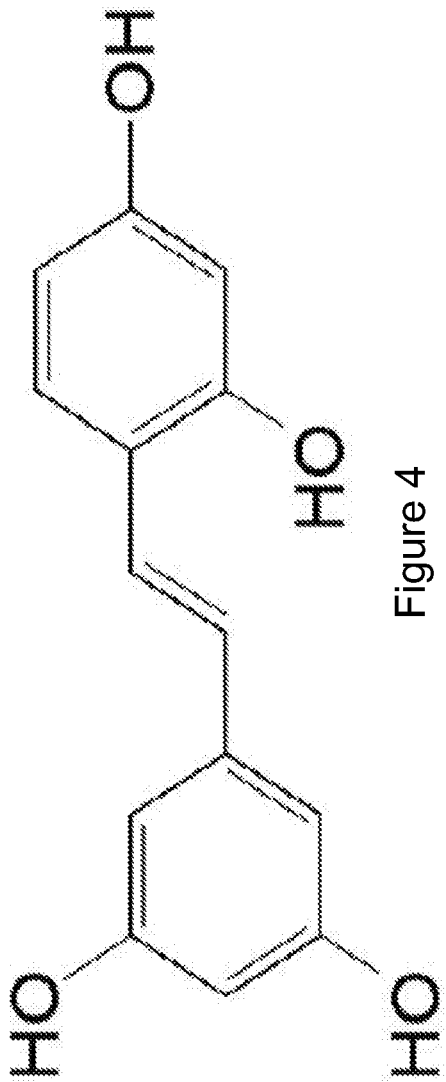
FIG. 4 shows the chemical structure of oxyresveratrol.

Immunosuppressive effects of peptide formulations and/or oxyresveratrol, are further noted. FIG. 3 shows the chemical structure of the decapeptide P4 of the SEQ ID NO: 9. FIG. 4 shows the chemical structure of oxyresveratrol.

In particular, the decapeptide-12 (P4) of SEQ ID NO: 9 and the oxyresveratrol exhibited anti-inflammatory effects as measured by two different methods:

1) blockade of stimulated peripheral blood mononuclear cells (PBMCs), and 2) inhibition of natural killer (NK)-mediated cytotoxic killing.

These results are now discussed in detail in the example below.

Example

PBMC Proliferation and NK Cytotoxic Killing Assays

Cryopreserved human PBMCs were purchased from Astarte Biologics (Redmond, Washington, USA), activated with phytohemagglutinin (PHA), and proliferation assessed. Interleukin (IL)-2 activated human NK cell cytotoxic killing of human K562 cells was assessed using a CytoTox96 non-radioactive cytotoxicity assay kit (Promega). Protease inhibitor was added to the media to prevent degradation of decapeptide-12.

Three independent trials were performed for each experiment. Microsoft Excel (Seattle, Washington) was used to calculate means and standard errors and statistical significance was determined using unpaired analysis of variance or two-tailed student T-test. P values <0.05 were taken to be statistically significant.

The effects of decapeptide-12 and oxyresveratrol on PBMC proliferation rates after exposure to PHA for 72 hours, were explored.

Figure 5:
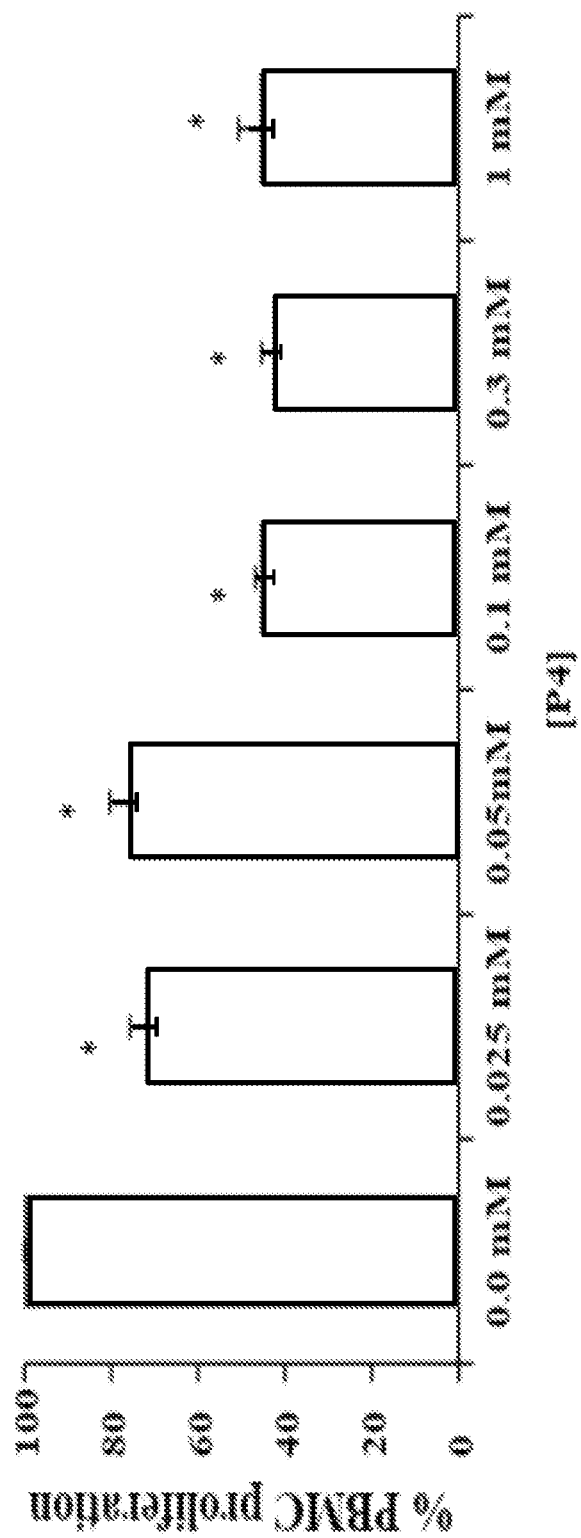
FIG. 5 is a plot of immunosuppressive effects of the decapeptide P4 of the SEQ ID NO: 9.

FIG. 5 plots the immunosuppressive effects of decapeptide-12 (P4) on PHA-stimulated PBMC proliferation. Data are expressed as percent (%) control and represent means±SEM of 3 separate experiments. *P<0.05. E:T denotes effector to target cell ratio.

FIG. 5 shows that decapeptide-12 statistically significantly (p<0.02) reduced proliferation by 28.0±3.8 percent at 0.05 millimolar and 54.3±1.1 at 0.1 millimolar. No significant additional reduction was achieved at 0.3 or 1 millimolar (p>0.05).

Figure 6:
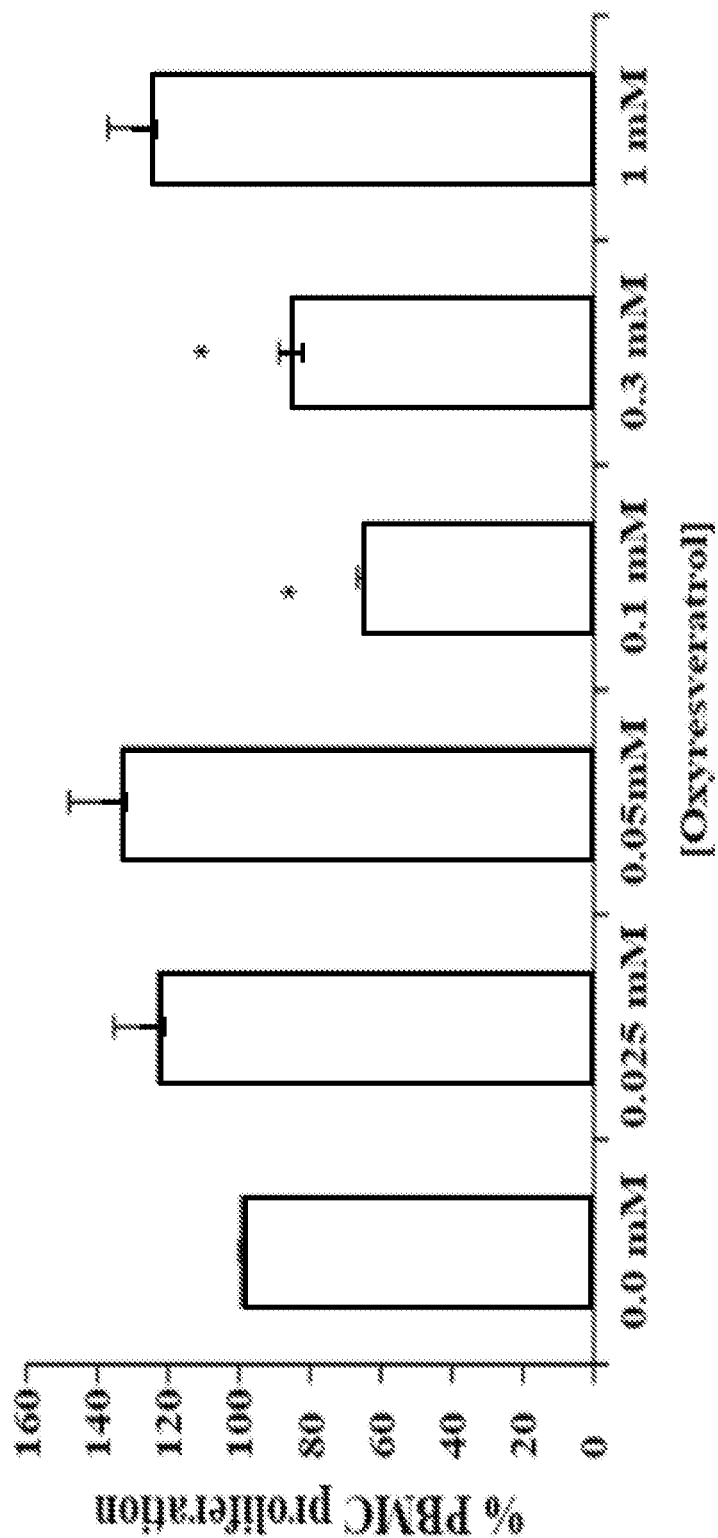
FIG. 6 is a plot of immunosuppressive effects of oxyresveratrol.

FIG. 6 plots the immunosuppressive effects of oxyresveratrol on PHA-stimulated PBMC proliferation. Data are expressed as percent (%) control and represent means±SEM of three separate experiments. *$P<0.05$. E:T denotes effector to target cell ratio.

FIG. 6 shows that oxyresveratrol also reduced proliferation by 35.3±1.8 percent ($p<0.02$) at 0.1 millimolar, and by 14.7±3.4 percent at 3 millimolar ($p<0.02$).

The impact of decapeptide-12 on IL-2 primed NK-mediated cytotoxic killing of K562 cells, was also assessed.

Figure 7:
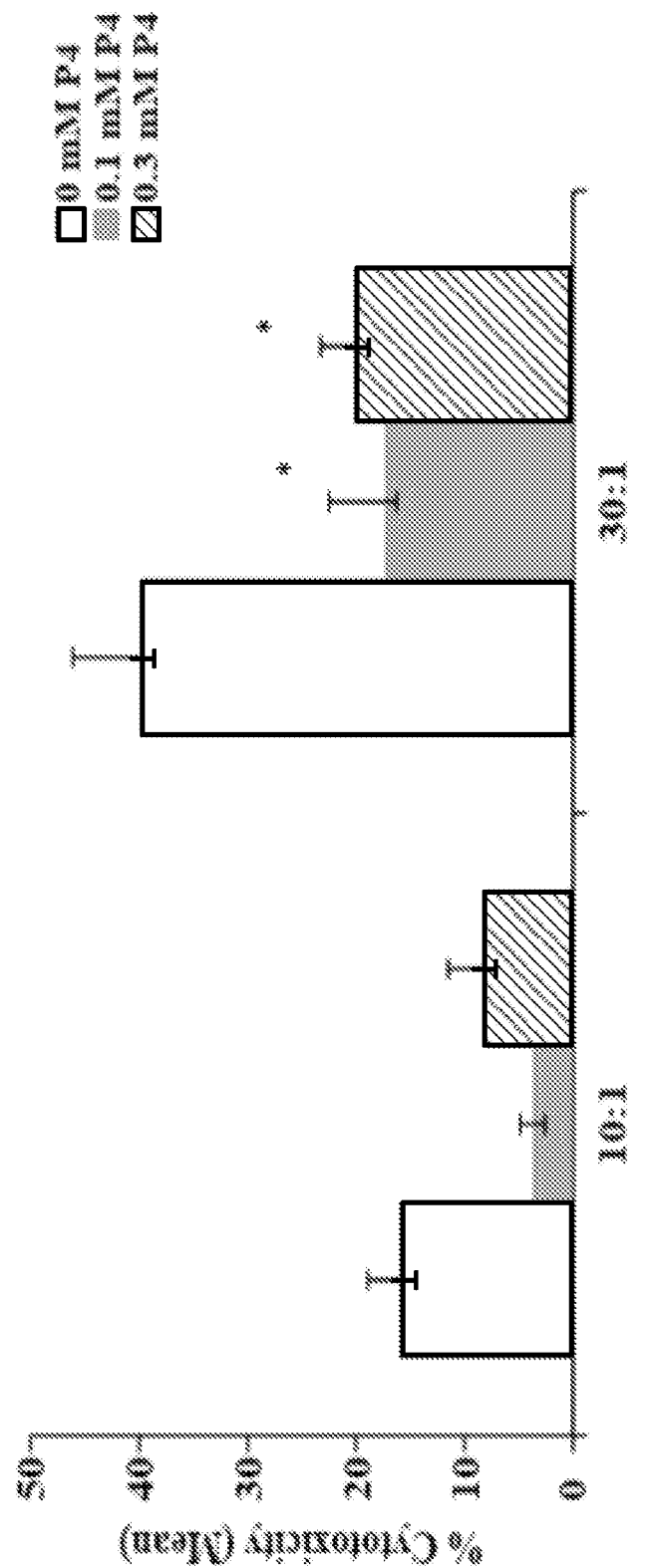
FIG. 7 is a plot of immunosuppressive effects of the decapeptide P4 of the SEQ ID NO: 9.

FIG. 7 plots the immunosuppressive effects of decapeptide-12 (P4) on NK92-mediated cytotoxic killing of K562 cells. Data are expressed as percent (%) control and represent means±SEM of 3 separate experiments. *$P<0.05$. E:T denotes effector to target cell ratio.

FIG. 7 illustrates that decapeptide-12 reduced NK killing by 81.4±1.3 percent and 59.3±3.6 percent at 0.1 and 0.3 millimolar, respectively ($p>0.05$), at 10:1 ratio of effector to target (E:T) cells. At a 30:1 ratio, decapeptide-12 reduced NK killing by 64.8±5.3 percent and 44.8±3.2 percent at 0.1 and 0.3 millimolar, respectively ($p<0.04$).

Figure 8:
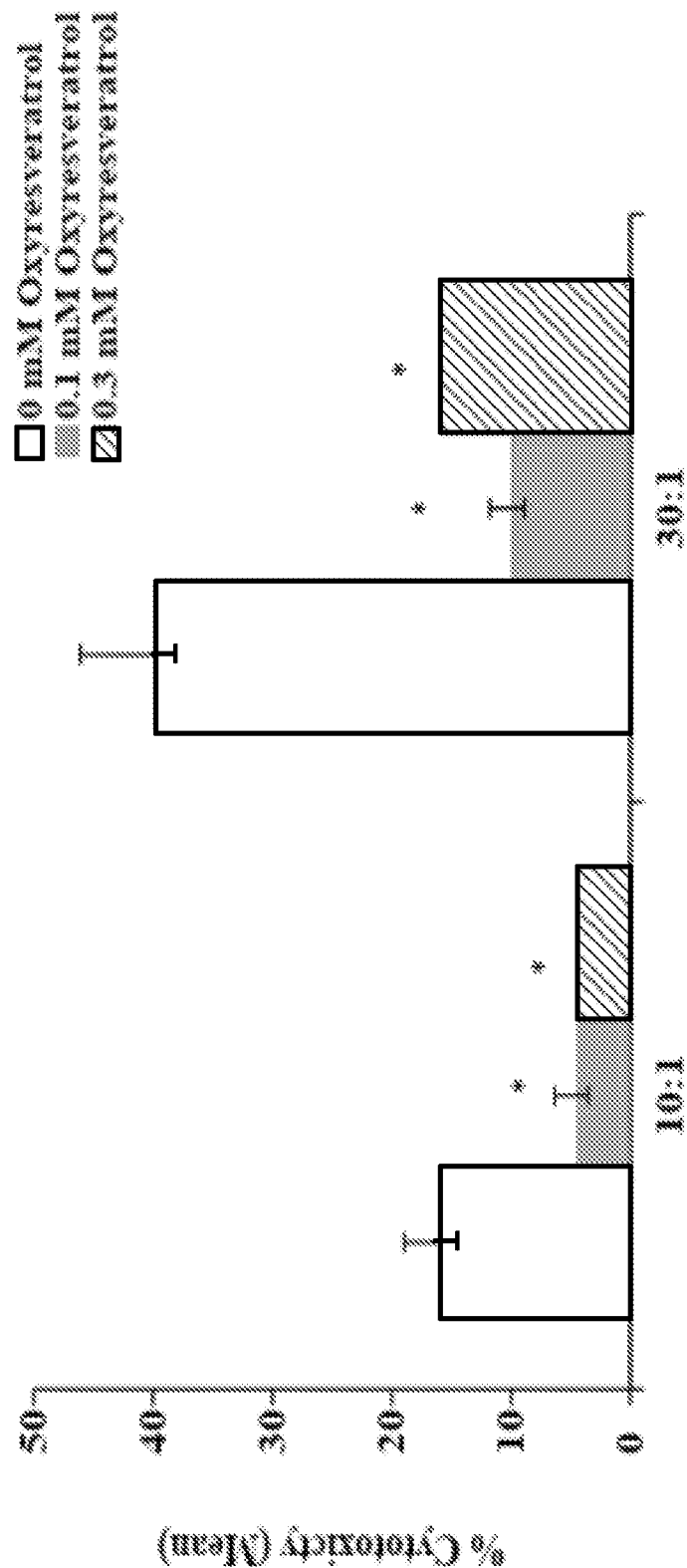
FIG. 8 is a plot of immunosuppressive effects of oxyresveratrol.

FIG. 8 plots the immunosuppressive effects of oxyresveratrol on NK92-mediated cytotoxic killing of K562 cells. Data are expressed as percent (%) control and represent means±SEM of three separate experiments. *$P<0.05$. E:T denotes effector to target cell ratio.

FIG. 8 shows that oxyresveratrol diminished NK killing by 88.7±1.8 percent and 86.1±0.9 percent at 0.1 and 0.3 millimolar, respectively ($p<0.03$), at E:T ratio of 10:1. At a 30:1 ratio, oxyresveratrol blocked NK killing by 72.8±1.9 percent and 64.0±3.4 percent at 0.1 and 0.3 millimolar, respectively ($p<0.03$).

Thus, studies showed that the decapeptide-12 and the oxyresveratrol exhibit an anti-inflammatory effect as measured by two methods: 1) blockade of PHA-stimulated PBMC proliferation, and 2) inhibition of NK-mediated cytotoxic killing.

For the blockade of proliferation test, the effect of decapeptide-12 appeared dose-dependent. The effect of oxyresveratrol exhibited a limited inhibitory concentration range.

In fact, the general trend showed oxyresveratrol may have biphasic effects. This is because concentrations of 0.3 and 1 millimolar showed progressively less inhibition than at a concentration of 0.1 millimolar.

The decapeptide-12 exhibited a plateau or maximum inhibition at 0.1 millimolar or greater in the concentration range tested. This may be explained by dose-dependent differences in activation of downstream signaling pathways or feedback loops. Indeed, careful examination of dose-dependency curves of sirtuin expression patterns reveal biphasic effects with higher concentrations becoming inhibitory.

In contrast, abrogation of NK killing appeared dose-dependent for both decapeptide-12 and oxyresveratrol. Oxyresveratrol showed more pronounced inhibition at all concentrations tested.

The inhibitory effects were greater at an E:T ratio of 10:1 than 30:1 for both decapeptide-12 and oxyresveratrol. This may be due to blockade of NKG2D and perforin mediated cytotoxicity.

It is noted that resveratrol (an analog of oxyresveratrol) inhibits PHA-induced proliferation at 0.1 millimolar. This suppression effect may be due to inhibition of NF-kappa B which is also regulated by sirtuins and linked to immune and inflammatory responses as well as regulation of cell proliferation and apoptosis, amongst other effects.

Taken together, the immunosuppressive effects observed here suggest that unique and specific regulatory pathways are engaged in different arms of the immune system. Further studies may clarify these pleiotropic effects.

For example, assessment of the impact of these two agents on pro-inflammatory mediators such as TNFα, IL-1β, IFNγ, and IL-6 could be insightful. In addition, determination of translational and other transcriptional effects of activated versus resting PBMCs could be insightful.

While the above description mentions a typical decapeptide concentration of between about 0-1.0 millimolar in noting where the effect was evident, different concentrations may have a positive effect. Thus some embodiments may utilize a decapeptide concentration of 1.0 millimolar or greater. Examples of peptide concentration ranges according to various embodiments are 0.025 millimolar, 0.05 millimolar, 0.1 millimolar, 0.2 millimolar, 0.3 millimolar, 0.4 millimolar, 0.5 millimolar, 0.6 millimolar, 0.7 millimolar, 0.8 millimolar, 0.9 millimolar, and 1.0 millimolar or greater.

And while the above description mentions a typical oxyresveratrol concentration of between about 0.1-1.0 millimolar in noting where the effect was evident, different concentrations may have a positive effect. Thus some embodiments may utilize an oxyresveratrol concentration of 1.0 millimolar or greater. Examples of oxyresveratrol concentration ranges according to various embodiments are 0.1 millimolar, 0.2 millimolar, 0.3 millimolar, 0.4 millimolar, 0.5 millimolar, 0.6 millimolar, 0.7 millimolar, 0.8 millimolar, 0.9 millimolar, and 1.0 millimolar or greater.

It is further noted that a particular component (e.g., decapeptide, oxyresveratrol) may be used in combination with another component(s) in order to achieve the desired effect. For example, a particular decapeptide could be used in combination with other peptides such as decapeptides P4A, 4B, and/or 4C and/or with other components such as oxyresveratrol. According to such embodiments, a synergistic effect realized by including other components may ultimately reduce the concentration of any individual component (e.g., decapeptide, oxyresveratrol, other) that is needed to achieve the desired result.

While the above specifically includes decapeptides and oxyresveratrol as possible additional components, embodiments are not limited to this. Examples of other possible additives can include but are not limited to, α-lipoic acid, biotin, caffeine, ceramides, coenzyme Q10, glycolic acid, green tea, human stem cells, human stem cell extracts, hyaluronic acid, hydroquinone, jojoba oil, kojic acid, lactic acid, malic acid, niacinamide, oligopeptides, peptides, plant stem cells, plant stem cell extracts, resveratrol, retinol, vitamin C, vitamin E, and vitamin K, amongst others.

It is noted that different embodiments may be utilized for immunosuppression of a variety of skin cell types. Examples of terminally differentiated skin cells can include but are not limited to keratinocytes, fibrocytes, melanocytes, and immune cells such as langerhans cells (e.g., histiocyte or dendrocytes) that age over time as well.

Certain embodiments may also be utilized to treat skin progenitor cells for immunosuppression and reduction in skin aging and allow for skin renewal over its lifetime. Examples of such progenitor cells may include but are not limited to epidermal keratinocyte progenitors, fibroblasts, melanoblasts, histioblasts, or dendroblasts which are progenitors for langerhans cells that lodge in the epidermis.

While the above description has focused upon the treatment of human skin cells, specific embodiments are not limited to such approaches. Alternative embodiments could employ the treatment of skin cells from other organisms, including but not limited to mammals such as cows (e.g., in the manufacture of leather from skin), pigs, and other animals (e.g., dogs, cats, and others that may be valued based upon skin appearance for contest purposes).

Moreover, while the above description has focused upon treatment of skin cells, embodiments are not limited to this or any other type of cell. Some embodiments may treat various types of mammalian and even non-mammalian cells.

And, according to some embodiments, treatment could occur via oral administration to a mammalian subject. Alternatively, treatment could involve other forms of delivery, such as direct application or targeted local application (e.g., injection).

Clause 1B. A method of treating a subject by performing immunosuppression of a cell, the method comprising administering to a subject in need thereof a composition comprising an effective amount of one or more peptides, wherein the one or more peptides comprise, SEQ ID NO: 9, SEQ ID NO: 10, SEQ ID NO: 11, or SEQ. ID NO: 12.

Clause 2B. The method according to clause 1B wherein the peptide consists of SEQ ID NO: 9.

Clause 3B. The method according to clause 1B wherein the peptide consists of SEQ ID NO: 9 modified by a modifying group, the modifying group being either a palmitoyl group or an acetyl group at an amino-terminal end, or amidation of a carboxy-terminal end, or both.

Clause 4B. The method according to clause 1B wherein the peptide consists of SEQ ID NO: 11 having a tyrosine amino acid at a position 6 as a D-isoform, and all other amino acids being L-isoforms.

Clause 5B. The method according to clause 1B wherein the cell is a mammalian cell.

Clause 6B. The method according to clause 5B wherein the mammalian cell is a skin cell.

Clause 7B. The method according to clause 6B wherein the mammalian skin cell is a progenitor.

Clause 8B. The method according to clause 7B wherein the progenitor is an epidermal keratinocyte progenitor, a melanoblast, a fibroblast, a histioblast, or a dendroblast.

Clause 9B. The method according to any of clauses 1B, 5B, 6B, 7B, and 8B wherein the administration is by oral administration.

Clause 10B. The method according to clause 1B wherein the cell is terminally differentiated.

Clause 11B. The method according to clause 10B wherein the cell is a keratinocyte, a melanocyte, a fibrocyte, a histiocyte, or a dendrocyte.

Clause 12B. The method according to clause 1B wherein the peptide is present in a concentration of about 1 millimolar or less.

Clause 13B. The method according to clause 1B wherein the composition further comprises oxyresveratrol.

Clause 14B. A method of treating a subject by performing immunosuppression of a cell, the method comprising administering to a subject in need thereof a composition comprising an effective amount of oxyresveratrol.

Clause 15B. The method according to clause 14B wherein the oxyresveratrol is present in a concentration of between about 0.1-1.0 millimolar.

Clause 16B. The method according to clause 14B wherein the composition further comprises an effective amount of one or more peptides, wherein the one or more peptides comprise SEQ ID NO: 9, SEQ ID NO: 10, SEQ ID NO: 11, or SEQ. ID NO: 12.

Clause 17B. The method according to clause 16B wherein the peptide consists of SEQ ID NO: 9.

Clause 18B. The method according to clause 16B wherein the peptide is present in a concentration of about 1 millimolar or less.

Clause 19B. The method according to clause 14B wherein the cell is a mammalian cell.

Clause 20B. The method according to clause 19B wherein the mammalian cell is a skin cell.

Clause 21B. The method according to clause 20B wherein the mammalian skin cell is a progenitor.

Clause 22B. The method according to clause 21B wherein the progenitor is an epidermal keratinocyte progenitor, a melanoblast, a fibroblast, a histioblast, or a dendroblast.

Clause 23B. The method according to any of clauses 14B, 19B, 20B, 21B, and 22B wherein the administration is by oral administration.

Clause 24B. The method according to clause 14B wherein the cell is terminally differentiated.

Clause 25B. The method according to clause 24B wherein the cell is a keratinocyte, a melanocyte, a fibrocyte, a histiocyte, or a dendrocyte.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. A method of immunosuppressing a cell in a subject, the method comprising administering to a subject in need thereof a composition comprising an effective amount of one or more peptides, wherein the one or more peptides comprise SEQ ID NO: 9, SEQ ID NO: 10, SEQ ID NO: 11, or SEQ ID NO: 12;
   wherein the immunosuppressing comprises at least one of inhibiting natural killer (NK)-mediated cytotoxic killing, and inhibiting proliferation of peripheral blood mononuclear cells (PBMCs).

2. The method according to claim 1, wherein the peptide consists of SEQ ID NO: 9.

3. The method according to claim 1, wherein the cell is a mammalian cell.

4. The method according to claim 3, wherein the mammalian cell is a skin cell.

5. The method according to claim 4, wherein the mammalian skin cell is a progenitor.

6. The method according to claim 5, wherein the progenitor is an epidermal keratinocyte progenitor, a melanoblast, a fibroblast, a histioblast, or a dendroblast.

7. The method according to claim 1, further comprising orally administering the composition.

8. The method according to claim 1, wherein the cell is terminally differentiated.

9. The method according to claim 8, wherein the cell is a keratinocyte, a melanocyte, a fibrocyte, a histiocyte, or a dendrocyte.

10. The method according to claim 1, wherein the peptide is present in a concentration of about 0.025 millimolar to about 1 millimolar.

11. The method according to claim 1, wherein the composition further comprises oxyresveratrol.

12. The method of claim 1, wherein the immunosuppressing a cell in the subject reduces skin aging and enables skin renewal in the subject.

13. The method of claim 12, wherein the immunosuppressing a cell in the subject enables skin renewal in the subject.

\* \* \* \* \*